(12) United States Patent
Ajayan et al.

(10) Patent No.: US 9,095,639 B2
(45) Date of Patent: Aug. 4, 2015

(54) ALIGNED CARBON NANOTUBE-POLYMER MATERIALS, SYSTEMS AND METHODS

(75) Inventors: Pulickel M. Ajayan, Clifton Park, NY (US); Ali Dhinojwala, Akron, OH (US)

(73) Assignee: The University of Akron, Akron, OH (US)

(*) Notice: Subject to any disclaimer, the term of this patent is extended or adjusted under 35 U.S.C. 154(b) by 971 days.

(21) Appl. No.: 11/675,442

(22) Filed: Feb. 15, 2007

(65) Prior Publication Data
US 2008/0280137 A1    Nov. 13, 2008

Related U.S. Application Data

(63) Continuation-in-part of application No. 11/428,185, filed on Jun. 30, 2006.

(51) Int. Cl.
*B29D 22/00* (2006.01)
*B29D 23/00* (2006.01)
(Continued)

(52) U.S. Cl.
CPC ......... *A61L 24/0078* (2013.01); *B81C 1/00206* (2013.01); *C08K 7/24* (2013.01);
(Continued)

(58) Field of Classification Search
USPC ................. 428/364, 34.1, 35.7, 36.9, 401; 977/778, 734, 742, 750, 752, 753; 623/1.1, 1.11, 1.15
See application file for complete search history.

(56) References Cited

U.S. PATENT DOCUMENTS

2003/0165418 A1*  9/2003  Ajayan et al. ............. 423/447.2
2004/0058153 A1*  3/2004  Ren et al. .................... 428/408
(Continued)

FOREIGN PATENT DOCUMENTS

JP    2007-536101    12/2007

OTHER PUBLICATIONS

Aligned Carbon Nanotube-Polymer Hybrid Architectures for Diverse Flexible Electronic Applications, Yung Joon Jung et al., Nano Letters, 2006, vol. 6, No. 3, pp. 413-418.
Synthetic gecko foot-hairs from multiwalled carbon nanotubes, Betul Yurdumakan et al., Chemical Communication, The Royal Society of Chemistry 2005, pp. 3799-3801.
(Continued)

*Primary Examiner* — Matthew Matzek
(74) *Attorney, Agent, or Firm* — Renner Kenner Greive Bobak Taylor & Weber (57) ABSTRACT

The invention is directed to carbon nanostructure composite systems which may be useful for various applications, including as dry adhesives, electronics and display technologies, or in a wide variety of other areas where organized nanostructures may be formed and integrated into a flexible substrate. The present invention provides systems and methods wherein organized nanotube structures or other nanostructures are embedded within polymers or other flexible materials to provide a flexible skin-like material, with the properties and characteristics of the nanotubes or other nanostructures exploited for use in various applications. In one aspect, the invention is directed to a carbon nanotube/polymer composite material having a plurality of carbon nanotubes formed into a predetermined architecture, with each of the plurality of nanotubes having a desired width and length. The architecture of the plurality of nanotubes defines at least one orientation for a plurality of nanotubes, and also defines the approximate spacing between nanotubes and/or groups of nanotubes. The carbon nanotube architecture is at least partially embedded with a polymer matrix in a manner that the architecture is stabilized in the predetermined architecture. The polymer matrix may also be formed to have a desired predetermined thickness.

20 Claims, 8 Drawing Sheets

(51) Int. Cl.
| | |
|---|---|
| *B32B 1/08* | (2006.01) |
| *A61L 24/00* | (2006.01) |
| *C08K 7/24* | (2006.01) |
| *C09J 7/00* | (2006.01) |
| *H01J 1/304* | (2006.01) |
| *H01J 9/02* | (2006.01) |
| *B81C 1/00* | (2006.01) |
| *B82Y 30/00* | (2011.01) |

(52) U.S. Cl.
CPC . *C09J 7/00* (2013.01); *H01J 1/304* (2013.01); *H01J 9/025* (2013.01); *B82Y 30/00* (2013.01); *C08K 2201/011* (2013.01); *C09J 2201/626* (2013.01); *H01J 2201/30469* (2013.01); *H01J 2329/0455* (2013.01); *Y10T 428/298* (2015.01); *Y10T 428/2933* (2015.01)

(56) References Cited

U.S. PATENT DOCUMENTS

| | | | |
|---|---|---|---|
| 2006/0068195 A1 | 3/2006 | Majumdar et al. | |
| 2006/0073332 A1* | 4/2006 | Huang et al. | 428/367 |
| 2006/0078725 A1 | 4/2006 | Fearing et al. | |
| 2008/0081176 A1* | 4/2008 | Huang et al. | 428/323 |
| 2008/0292840 A1 | 11/2008 | Majumdar et al. | |
| 2010/0098904 A1* | 4/2010 | Dai et al. | 428/119 |

OTHER PUBLICATIONS

Temperature-Activated Interfacial Friction Damping in Carbon Nanotube Polymer Composites, Jonghwan Suhr et al., Nano Letters, 2006, vol. 6, No. 2, pp. 219-223.

Bottom-Up Growth of Carbon Nanotube Multilayers: Unprecedented Growth, Xuesong Li et al., Nano Letters, 2005, vol. 5, No. 10, pp. 1997-2000.

Super-Compressible Foamlike Carbon Nanotube Films, Anyuan Cao, et al., Science, vol. 310, Nov. 25, 2005, pp. 1307-1310.

Substrate-site selective growth of aligned carbon nanotubes, Z. J. Zhang et al., Applied Physics Letters, vol. 77, No. 23, Dec. 4, 2000, pp. 3764-3766.

Interfacial energy and strength of multiwalled-carbon-nanotube-based dry adhesive, Yang Zhao et al., J. Vac. Sci. Technol. B 24(1), Jan./Feb. 2006, 2006 American Vacuum Society, pp. 331-335.

Masarapu, Charan and Wei Bingqing, Direct Growth of Aligned Multiwalled Carbon Nanotubes on Treated Stainless Steel Substrates, American Chemical Society, 2007, pp. 9046-9049, vol. 23, Langmuir, Newark, Delaware.

Lau, Kenneth K. S. et al., Superhydrophobic Carbon Nanotube Forests, Nano Letters, 2003, pp. 1701-1705, vol. 3, No. 12, Cambridge, MA.

International Application No. PCT/US2009/064296 International Search Report/Written Opinion, May 31, 2010, 12 pages.

* cited by examiner

ALIGNED CARBON NANOTUBE-POLYMER MATERIALS, SYSTEMS AND METHODS

FIELD OF INVENTION

The present invention relates to composite carbon nanostructures, such as nanotubes, integrated with a polymer matrix for providing diverse systems for different applications, such as dry adhesives, electronic systems, display devices and other applications. The invention is also directed to methods for forming such composite materials and for their use.

BACKGROUND OF THE INVENTION

The use and development of carbon nanotubes has expanded, as these materials have shown to be valuable in next generation industries including the fields of electronics and chemistry. The further development of carbon nanotube technology allows organized structures or intertwined randomly oriented bundles of carbon nanotubes to be formed. Techniques have been developed to controllably build organized architectures of nanotubes having predetermined orientations, such as vertically aligned nanotubes. Although such structures may be useful for a variety of purposes, the structures by themselves may be limited in terms of function and application.

In the area of adhesives for example, it would be desirable to provide dry adhesives which may be useful in a variety of applications and environments for which standard adhesives have deficiencies. Adhesives are typically wet and polymer-based, and have low thermal and electrical conductivity. For electronics, micro-electro-mechanical systems (MEMS), low or zero atmosphere environments, cryogenic or high temperature environments, or a variety of other areas, it would be desirable to provide a dry adhesive which is selectively attachable and detachable to/from a surface. It would also be desirable to provide an adhesive which has other beneficial properties, such as high electrical and thermal conductivity or high adhesion strengths while being selectively detachable. For example, the mechanism which allows a gecko lizard to climb a vertical surface or any other surface is based upon the anatomy of the gecko's feet and toes, wherein each five-toed foot is covered with microscopic elastic hairs called setae. The ends of these hairs split into spatulas which come into contact with the surface and induce enough intermolecular (van der WAALS, [VdW]) forces to secure the toes to the surface. The gecko's foot anatomy allows them to selectively adhere to any surface which they touch. Although attempts have been made to provide synthetic systems which mimic the gecko's feet and toe anatomy, no such systems have generally been successful. It would be desirable to provide an adhesive which mimics these characteristics, and provides a surface which interacts with other surfaces via intermolecular or VdW forces, via nanostructure technologies.

In a variety of other areas, the use of organized carbon nanostructures in unique configurations may provide valuable functions in biocompatible or bioactive systems, electronic displays, functional films or skins, or other applications.

SUMMARY OF THE INVENTION

The present invention is therefore directed to carbon nanostructure composite systems which may be useful for various applications, including as dry adhesives, electronics and display technologies biosystems, or in a wide variety of other areas where organized nanostructures may be formed and integrated into a flexible substrate. The present invention provides systems and methods wherein organized nanotube structures or other nanostructures are embedded within polymers or other flexible materials to provide a flexible skin-like material, with the properties and characteristics of the nanotubes or other nanostructures exploited for use in various applications.

In one aspect, the invention is directed to a carbon nanotube/polymer composite material having a plurality of carbon nanotubes formed into a predetermined architecture, with each of the plurality of nanotubes having a substantially predetermined width and length. The architecture of the plurality of nanotubes defines at least one orientation for a plurality of nanotubes, and also defines the approximate spacing between nanotubes and/or groups of nanotubes. The carbon nanotube architecture is at least partially embedded with a polymer matrix in a manner that the architecture is stabilized in the predetermined architecture. The polymer matrix may also be formed to have a substantially predetermined thickness.

Another aspect of the invention is directed to a method of forming a carbon nanostructure/polymer composite material by the steps of providing a substrate having a predetermined configuration, and providing a plurality of carbon nanotubes or other nanostructures formed into a predetermined architecture supported on the substrate. At least one polymeric polymer precursor is introduced onto the substrate in a manner to embed the predetermined nanotube architecture at least partially therein. Thereafter, the at least one precursor is polymerized so as to fix the carbon nanotubes in position and stabilize the predetermined architecture. The step of providing the plurality of carbon nanotubes may further design the nanotubes to have a substantially predetermined width and length, as well as defining at least one orientation for a plurality of nanotubes. The spacing between nanotubes and/or groups of nanotubes may also be controlled. The carbon nanotube architecture is at least partially embedded with a polymer matrix in a manner that the architecture is stabilized, and the polymerized matrix may be formed to have a substantially predetermined thickness.

The invention is also directed to methods and systems wherein multi-walled carbon nanotubes (MWNT) are constructed on polymer surfaces or partially within polymer films with strong nanometer level adhesion similar to or stronger than gecko foot-hairs.

The invention also relates to the use of carbon nanostructures integrated into a polymer matrix for providing bioactive or biocompatible systems for use with biological organisms or systems.

The invention is also directed to the use of organized nanostructures such as MWNT structures, in combination with flexible materials to form field emission displays on flexible substrates. Other flexible surfaces or coatings may be provided for use in a variety of other applications, such as a skin or coating on the surface of a vehicle or aircraft, wherein the characteristics of the carbon nanotubes can provide for properties of anti-friction, anti-static and non-wetting for example.

For adhesive type applications, the invention provides a patterned nanotube surface with microscopic features which together provide very strong adherence forces on virtually any surface. The features include, in examples, a hierarchical structure of both larger nanotube structures in combination with smaller nanotube structures. An adhesive nanotube flexible tape may be formed, which can perform over and over again, with very high adhesion characteristics.

The invention also relates to the method of making a flexible nanotube device, with an array or architecture of nanotubes being embedded in and functioning in association with a flexible substrate. Methods for embedding or transferring nanotube structures in the flexible substrate or matrix may include but are not limited to, using a molten material interface, using a prepolymer and crosslinking, using a monomer selectively polymerized by applying stimulant, using a selectively degradable substance, or using a viscous material.

Other aspects and advantages of the invention will become apparent upon a reading of the description of the present invention in conjunction with the drawings.

DETAILED DESCRIPTION OF THE INVENTION

Figure 1:
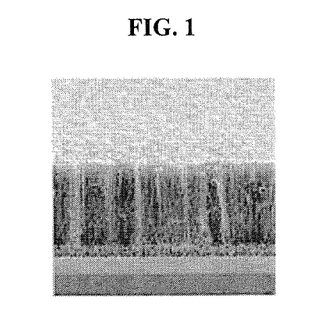
FIG. 1 is a scanning electron microscope image of vertically aligned multi-walled carbon nanotube structures.

Turning now to the FIGS., a first embodiment of a carbon nanostructure/polymer composite material according to the invention will be described with reference to FIGS. 1-4, wherein a large number of carbon nanostructures, such as multi-walled carbon nanotubes (MWNT) 10 are formed on a substrate 12 as shown in FIG. 1. The growth of vertically aligned MWNT 10 on a substrate 12, such as silicon substrate, may be performed in any suitable manner, with various approaches having been developed. Alternatively, the nanostructures may be single-walled nanotubes, or nanosheets or other nanostructures formed of carbon.

One method is to selectively grow carbon nanotubes on silica templates located on a silicon substrate at set forth in Z. J. Zhang, B. Q. Wei, G. Ramanath, P. M. Ajayan, Appl. Phys. Lett. 77, 3764 (2000), which is hereby incorporated herein by reference. The use of this template structure is advantageous in that it does not require the deposition and patterning of a catalyst material on the substrate 12, although such an approach may also be used according to the invention. Another method may be as described in published U.S. Patent Application 2003/0165418, which is incorporated by reference herein. Any other suitable methods to provide organized architectures of carbon nanotubes on a substrate are also contemplated and within the scope of the invention. The substrate 12 may be formed of other materials such as quartz, molybdenum, or other suitable materials. Further, the carbon nanostructures may be formed by other suitable techniques, such a by plasma enhanced chemical vapor deposition, or any other suitable technique. Such processes may form other carbon nanostructures, such as nanofibers, sheets, pillars or other forms. The carbon nanotubes or other carbon nanostructures also have good mechanical properties such as very high Young's modulus and very high tensile and bending strengths, making them useful for the applications as described herein.

Figure 2:
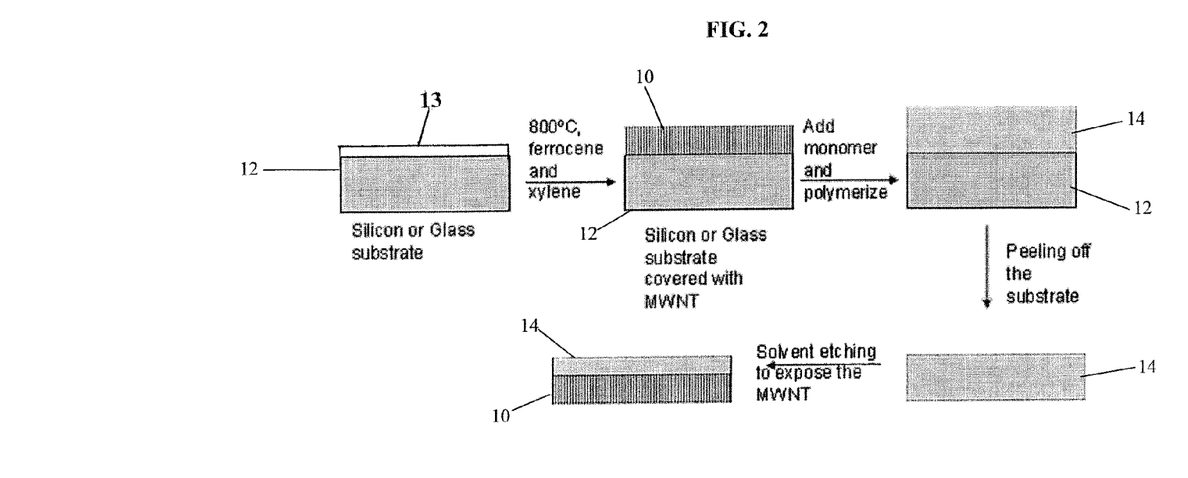
FIG. 2 is a schematic illustration of a method for preparing a carbon nanotube-polymer composite according to the invention.

Turning now to FIG. 2, a first method for producing a carbon nanotube-polymer composite according to the invention is shown. In this example, the growth of nanotubes on a silicon substrate may be accomplished through chemical vapor deposition (CVD). A gaseous mixture of ferrocene (0.3 g), is used as a catalyst source, and xylene (30 mL), is used as a carbon source. Other suitable materials may be used if desired. The gaseous mixture is heated to over 150° C. and passed over the substrate 12 for ten minutes, with the substrate 12 itself being heated to approximately 800° C. in a quartz tube furnace. The substrate 12 may be provided with an oxide layer 13 on which MWNT 10 grow with controlled thickness and length. If desired, the oxide layer of the substrate 12 can be patterned by photolithography or other suitable techniques, and may be followed by a combination of wet and/or dry etching in order to create various predetermined patterns of the oxide layer 13 and correspondingly of the carbon nanotubes 10 grown thereon. After the oxide layer 13 of the substrate 12 is covered with MWNT to form a desired and predetermined architecture of carbon nanostructures, the sample, with the MWNT side facing up, has at least one polymeric polymer precursor material, such as at least one monomer, poured thereon to encase the carbon nanostructure architecture. Thereafter, the precursor materials are polymerized to embed the carbon nanostructures in a polymer matrix. For example, a methyl methacrylate monomer (60 mL) may be used, and then polymerized using a 2,2'-azobis (isobutyronitrile) initiator (0.17 g) and a 1-decanethiol chain transfer agent (30 μL) in a clean room. As seen in FIG. 2, the MWNT are then encapsulated within a polymer matrix 14 on substrate 12. The MWNT or other nanostructures and architectures are embedded and stabilized in the PMMA matrix 14, without disruption of the organized architecture of the carbon nanostructures as originally grown or provided on substrate 12. To facilitate maintaining the desired architecture of the carbon nanotubes or other nanostructures, the introduction of the monomer or other precursors is performed in a manner to flow around the nanotube architecture without forcing the nanotubes together or otherwise significantly disrupting their position and orientation on the substrate 12. Similarly, polymerization is completed without disruption of the nanotube architecture, with properties controlled to maintain the desired configuration. For example, polymerization may be performed in a manner to reduce possible effects of evaporation upon the matrix 14 and ultimately the carbon nanotubes embedded therein. After completion of polymerization in a water bath at 55° C. for 24 hours, the matrix 14 may simply be peeled from the substrate 12 forming a flexible skin-like sheet in which the carbon nanotubes 12 are fully or partially embedded and stabilized.

Polymeric matrix materials according to the invention may be of any suitable type, wherein polymeric polymer precursors may include monomers, dimers, trimers or the like. Monomers utilized in this invention may generally be selected from the family of vinyl monomers suitable for free radical polymerization under emulsion conditions. Non-limiting examples of suitable vinyl monomers include methacrylates, styrenes, vinyl chlorides, butadienes, isoprenes, and acrylonitriles, polyacrylic and methacrylic esters and any other suitable precursor materials. The matrix polymer may be a polymer of one or more of the following monomers: methyl methacrylate (MMA), other lower alkyl methacrylates (e.g. ethyl methacrylate, propyl methacrylate, isopropyl methacrylate, butyl methacrylate, 2-ethylhexyl methacrylate, etc., as an example. A starting monomer formulation may also include one or more polymerization initiators. These include, for example, benzoyl peroxide, lauryl peroxide, azobis (isobutyronitrile), 2,2'-azobis(2,4-dimethyl-4 methoxypropionitrile), and 2,2'-azobis(2-methylpropionitrile) or other suitable initiator materials. These are used in small amounts which are well known in the art. Any initiator that is suitable for free radical polymerization can be considered according to the invention. Further, the polymer matrix may also be modified using nanofillers as an example. Nanofillers are fillers having at least one dimension in the nanoscale (1-999 nm). Suitable fillers may include, without limitation, clay minerals, fibers, micro-spheres, and layered silicates. Such nanofillers may have their surfaces modified by surface functionalization with ionic groups or the like to provide desired interaction in the polymer matrix. Additional optional components may be present in the polymer matrix if desired, such as chain transfer agents, which are typical of free radical polymerizations, to facilitate the polymerization of the monomer or other polymerizable components. Other optional components that may facilitate use in various applications may include colorants, mold-release agents, and other known modifiers. The starting monomer formulation or mixture may also include a crosslinking agent, as for example ethylene glycol dimethacrylate or other difunctional (i.e., diolefinic) monomer or mixture thereof. The polymeric materials may also be thermoset plastics or other suitable epoxy type materials. Epoxy resins useful in the present invention can be monomeric or polymeric, saturated or unsaturated, aliphatic, cycloaliphatic, aromatic or heterocyclic, and they can be substituted if desired with other substituents besides the epoxy groups, e.g., hydroxyl groups, ether radicals, halogen atoms, and the like. Also, as will be described in relation to other embodiments, materials such as silicones may be used to integrate carbon nanostructures therein, such as poly(dimethylsiloxane) or PDMS. Many other suitable polymeric materials are contemplated as will be understood by those skilled in the art.

The invention may be used to form adhesive type of devices or materials, wherein the carbon nanotubes are partially embedded and stabilized within a flexible substrate or matrix. The methods for forming such a device include a variety of suitable approaches, and other suitable methods are contemplated. For example, the carbon nanotubes are partially embedded and stabilized using a molten interface. In such an example, a flexible material is heated to be molten, for example just above its melting temperature, and vertically aligned carbon nanotubes are brought in contact with the material so that a predetermined, generally small fraction of tubes is introduced into the molten substance. Thereafter, the material is allowed to cool below its melting point and the nanotube structures are partially embedded therewith. Another method may use a prepolymer, wherein a paste of prepolymer is provided and carbon nanotube structures are brought in contact with the surface so that only a part of carbon nanotube structure is inside the prepolymer. The prepolymer is then crosslinked, thus trapping one end of carbon nanotube structures in its matrix. Alternatively, a monomer, chosen such that it can be polymerized by applying stimulant for example, may be used. Carbon nanotubes are brought in contact with the monomer and polymerization was set to occur. On polymerization, the polymerized material held the carbon nanotube structures in place. Another method may use a degradable substance. In this example, a prepolymer/monomer/solution/melt type of material, capable of degrading under suitable conditions may be used to coat the carbon nanotube structures such that they form a thin layer on the carbon nanotube structures. Thereafter the matrix is exposed to suitable conditions that would degrade a portion of the substance thereby leaving exposed or open ends of carbon nanotubes. A further method may use a viscous material, wherein a thin layer of viscoelastic material is applied onto a flexible substance and brought in contact with carbon nanotubes. The carbon nanotubes stick to the flexible substance via the viscoelastic material.

The flexible (or rigid) matrix 14 may then be used for a variety of applications, with one such application being to form a flexible skin-like material which could be used as a dry adhesive, simulating gecko foot-hairs. In this example, an adhesive tape may be formed using an array or architecture of nanotubes or nanostructures formed in association with a flexible substrate. The nanostructures are formed in a hierarchical structure in which larger structures are combined with smaller structures which together provide strong adhesion characteristics. As an example of a dry adhesive tape, the invention provides for the transference of micro-patterned carbon nanotube arrays onto flexible polymer tape in a hierarchical structure. The dry adhesive tape according to an example can support a force (36 $N/cm^2$), being nearly four times higher than the adhesion characteristics of the gecko foot, and sticks to a variety of surfaces, including materials such as Teflon.

As examples, as shown in FIGS. 4A-D, the hierarchical structure may include micron-size structures formed by bundles of nanotubes or nanostructures 18, and nanometer-size structures 19 as shown in FIGS. 4E-F formed by individual nanotubes or smaller bundles thereof. In this embodiment, the nanometer-size structures 19 are integrated into the larger micron-size structures 18. Such a hierarchical structure enhances the macroscopic adhesion characteristics of the tape, and facilitates the translation of the weak van der Waals interactions of the structures into very strong aggregate attractive forces. Flexible adhesive tapes are indispensable in peoples daily lives, but adhesives using viscoelastic materials (wet adhesives) have various deficiencies, including degradation of the adhesion properties over time. The stickiness of the wet adhesive is time and rate dependent, and such materials cannot operate in different environments such as under vacuum. The invention provides a dry adhesive tape type material, which can be formed in any desired configuration, for use in such applications as space applications. Further, the dry adhesive tape according to the invention may be used for repeated attachment and detachment applications. On coming in contact with any surface, the hierarchical structures formed of nanotubes deform, enabling molecular contact over a larger area, and acting to translate the locally weak van der Waals (vdW) interactions into high attractive forces. The multi-scale structures, including the micron-size structures formed by bundles of nanotubes or nanostructures 18, and the nanometer-size structures 19, may use micro fabricated multi-walled carbon nanotubes (MWCNT), but other suitable nanomaterials are contemplated.

The architecture of nanostructures includes both nanometer length scales of structures in association with micrometer length scales of structures, which together achieve large macroscopic adhesion. For example, a cm2 area of the MWCNT patterns transferred on a flexible tape was found to support 36 N. Similar adhesion forces are obtained on both hydrophilic (mica and glass) and hydrophobic (Teflon) surfaces. These dry adhesive tape according to this example of the invention show desirable adhesion and peeling properties and provide a dry, conductive, reversible adhesive for use in a variety of applications such as microelectronics, robotics and space applications. FIGS. 4A-D show examples of aligned MWCNT, in SEM images, wherein the sizes of the micron-size structures formed by bundles or groups of nanotubes or nanostructures 18 may vary from 50 to 500 microns in width for example. Each of the micron-size structures 18, has integrated therein the nanometer-size structures 19 shown in FIGS. 4E-F for example. The structures 19 may comprise thousands of individual bundles of aligned MWCNT with an average diameter of 8 nm. For the nanometer-scale structures 19, the dimensions may vary from 1 to 30 nanometers in width. The features or structures 18 and 19 have shapes which may include but are not limited to square, circular, and hexagonal cross-sections. The features or structures 18 and 19 may thus have sizes may range from 5~1000 μm, with spacing between structures which may range from 5~500 μm as an example. The height of exposed CNT's may range from 10 μm~1000 μm as an example.

For various adhesive applications, the use of MWCNT to construct the nanomaterial structures may provide desired characteristics due to the strong nanometer-level adhesion that vertically aligned MWCNT materials exhibit, along with excellent mechanical properties. In the examples of FIGS. 4A-F, the micron scale structures 18 and nanometer scale structures were fabricated using a photolithography patterning process. A catalyst (Fe and Al) was deposited on a silicon substrate in patterned patches with dimensions shown in FIGS. 4A-F. The MWCNT were grown at 700-800° C. using a mixture of ethylene and hydrogen gas and the MWCNT grew only in the areas covered with the catalyst. The length of carbon nanotubes was controlled by the reaction time, and in these examples was around 200-500 um for the shown structures. The structures were then transferred to a flexible substrate as previously described.

Figure 5A:
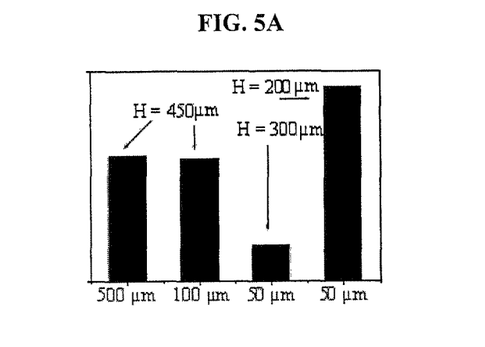
FIGS. 5A-5C show graphical representations of adhesion characteristics of a carbon nanotube/polymer composite material formed in accordance with an embodiment of the present invention, showing deflection-versus-displacement curves during loading-unloading cycles of a silicon probe engaging exposed carbon nanotubes associated with the composite as formed according to FIG. 2 or 3 as examples.
Figure 5B:
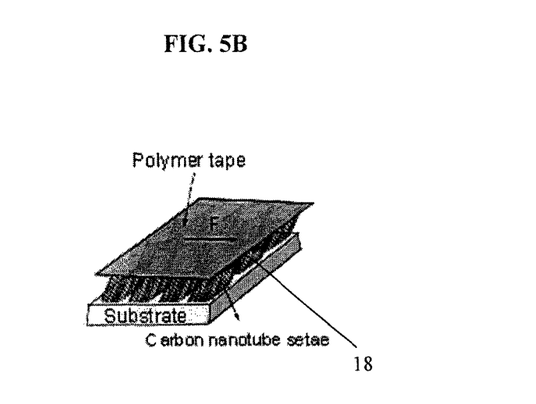

To measure the macroscopic adhesion forces, small areas of the formed flexible dry adhesive tapes were pressed against a smooth mica sheet. The force to peel the tape off the mica surface was measured. In FIG. 5A, the values for adhesion forces associated with a tape having the hierarchical structures discussed above are shown for various pattern sizes. The adhesion characteristics were found to be significantly higher than unpatterned nanotubes formed in a flexible substrate (not having the hierarchical structures). Further, with unpatterned nanotubes, the adhesion force is found to decrease with increases in contact area, such that support of larger weights may not be achieved by just increasing the contact area. To support larger forces, the hierarchical structure of micron size structures in combination with nanometer size features are found to avoid this potential limitation. FIG. 5A shows the measured adhesion at zero degree angle for the patterned CNT surfaces shown in FIGS. 4A-F by using hierarchical patterned surfaces with width features of 50 and 500 um, there was obtained a factor of 4-7 times higher adhesion forces as compared to the unpatterned surfaces of similar area. The adhesion forces came out to be 23 N/cm2 which is 2-3 times higher than the natural gecko foot-hairs for example. The advantages of hierarchical patterns became less prominent on reducing the patch size to 50 um (and 300 um in height) because decrease in the ratio of the width to height associated with the micron size structures makes them more mechanically weak. If a smaller height is used, such as 50 um structures 18 with a height of 200 um), an adhesion force of 36 N/cm2 was measured, being a factor of 4 times higher than the natural gecko setae for example. It is further found that the interfacial adhesion strength in these structures are likely even stronger than that measured using this peeling geometry. The 50-500 um patches of nanotubes made it possible to have the high force/area for larger areas, with similar force/area values obtained for dry adhesive tapes made with the hierarchical patterning having surface areas of 0.16 cm2 and 0.25 cm2 for example. As shown in FIG. 5B, the 50-500 um structures 18 deform and behave independently, thereby increasing the adhesion characteristics and hindering crack growth by providing resistance to the propagation of cracks.

Figure 5C:
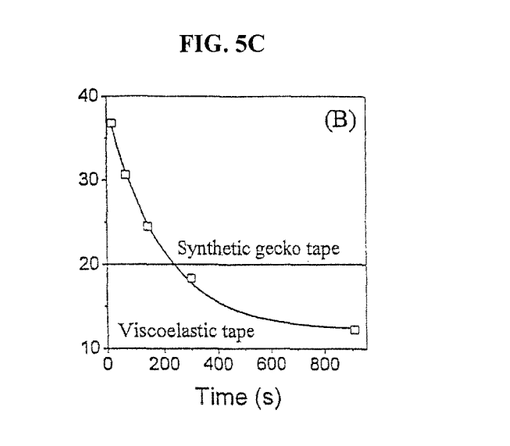

The adhesion characteristics of the dry adhesive tape according to examples of the invention are also thought to be based upon translation of the locally weak vdW forces to large attractive forces. Other forces on a microscopic scale may also be contributing, such as capillary forces due to humidity in the environment for example. The dry adhesive tape is found to adhere to both hydrophilic and hydrophobic surfaces. For example, on hydrophilic surfaces such as mica and glass (water wets both surfaces), a partially hydrophobic surface (coated with polymethylmethacrylate that shows a water contact angle of 70-80°) and a very hydrophobic surfaces (coated with poly(octadecyl acrylate) comb polymer that shows a water contact angle of 110°). Measurements on rough Teflon surfaces also show large adhesion forces at 0° angle that are comparable to those obtained for hydrophilic surfaces. Further, the adhesion based on vdW forces is time-independent as shown in FIG. 5C, distinct from a common viscoelastic based adhesive tape.

A further attribute of a dry adhesive tape according to the invention is found in that the tape offers very little resistance when peeled from a surface at an angle. For example, a dry adhesive tape using 500 um features 18 is found to peel off a mica substrate with an adhesive force of only 0.4 N/cm2 at 45° angle, 0.5 N/cm2 at a 30° angle, and 2.4 N/cm2 at a 10° angle. This peeling process resists any breaking or transfer of the MWCNT on the substrate and the dry adhesive tape can be reused many times without damage. The energy of detachment (G) can be calculated using $G=F(1-\cos\theta)/\text{width}$, where F is the peeling force and $\theta$ is the peeling angle. This equation is valid for peeling angles greater than 45°, and the elastic stiffness of the tape may facilitate at lower peeling angles. In examples according to the invention, G is 5 J/m2 on mica at a 45° peeling angle, being much larger than the thermodynamic work of adhesion. On Teflon substrates, G=2.2 J/m2 at 45° peeling angle consistent with the lower surface energy of Teflon in comparison to mica. The micron-size patterns 18 facilitate increasing the zone of deformation by bending the patterns and increasing the load bearing capacity during peeling. The dry adhesive tapes according to examples of the invention, using the hierarchical structures as described, with length scales of microns and nanometers are found to achieve higher adhesion forces, with the ability to adapt to desired adhesion characteristics by increasing the are of the tape.

It has also been found that the adhesion forces do not appear to be influenced by the chemical composition of the solid substrate in which the carbon nanotubes are partially embedded. The adhesive characteristics of the composite may thus provide uses as dry adhesives for microelectronics and low vacuum, cryogenic or high temperature applications, where typical adhesives cannot be used, or in a variety of other environments or applications. It should also be recognized that devices made according to the invention may allow separately formed composite materials according to the present invention to interact and adhere with one another. Alternatively, the nanostructures may be exposed on both surfaces of the composite so as to allow each surface to act as an adhesive surface. Further, in this and other embodiments, the composite material may also yield significant benefits in providing high thermal conductivity and/or insulation characteristics, which may be particularly important in electronics or other applications.

In examples of the dry adhesive tapes above, or in other examples, the ability to have portions of the nanotubes or other nanostructures exposed in a flexible matrix 14 enables interaction of the nanostructures with other surfaces or materials. As previously indicated, other methods for producing a composite having these characteristics are contemplated, such as the use of a solvent etching process to expose a portion of the MWNT 10, such as from the substrate-facing side of the matrix 14. For example, etching the top of a formed composite with a solvent such as acetone or toluene and subsequently washing with deionized water, will expose a predetermined length of the MWNT 10. The length of the nanotubes 10 which are exposed may be controlled by varying the solvent etching time as an example. Other suitable techniques for selectively exposing a length of the carbon nanotube fibers embedded within matrix 14 are contemplated as previously discussed. Thus, as should be evident, the particular nature of the exposed carbon nanotubes may be selectively controlled both upon growing or producing the nanotubes themselves and forming the architecture on substrate 12 as desired, as well as in selectively controlling the length and spacing of the exposed carbon nanotubes for various wide-ranging applications.

Figure 3:
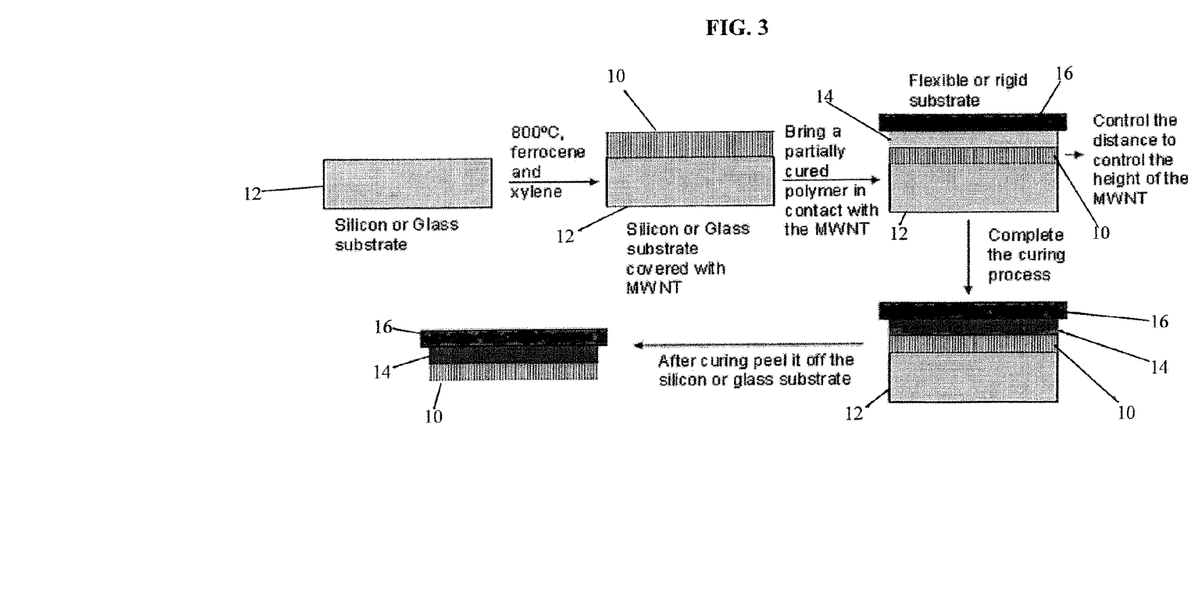
FIG. 3 is a schematic illustration of an alternative method for preparing a carbon nanotube-polymer composite according to the invention.
Figure 4:
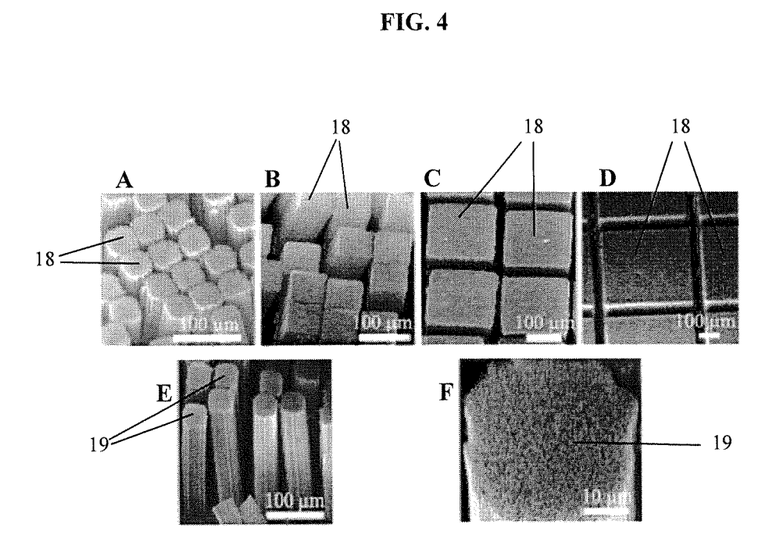
FIGS. 4A-4F show scanning electron microscope images of the carbon nanotube structures embedded in a polymer matrix and having a portion thereof exposed from the surface.

An alternative method for forming the composite according to the invention is shown in FIG. 3. Again, a substrate 12 may have an architecture of MWNT 10 grown thereon via an oxide layer or in any other suitable manner. Thereafter, a flexible or rigid substrate 16 provided with a partially cured polymeric material 14 disposed thereon is brought into contact with the MWNT 10 provided on substrate 12. In this example, the MWNT 10 are at least partially embedded within the partially cured polymer 14, without disruption of the position or orientation of the carbon nanotubes on substrate 12. The MWNT are only partially embedded within the polymer matrix 14, but are fully stabilized in their original and desired position as on substrate 12. Thereafter, the curing of the polymer 14 is completed in a manner to maintain the position of the partially exposed carbon nanotubes, and subsequent to curing, the assembly of the flexible or rigid substrate 16, and the polymer matrix including the partially embedded MWNT may be peeled from substrate 12. As shown in FIG. 3, a composite including the flexible or rigid substrate 16 and the polymer matrix 14 with partially exposed MWNT 10 is produced, which again may be used for a variety of applications. Similar to the embodiment of FIG. 2, the nanotube configurations and architectures, as well as the length of the exposed nanotubes may be precisely controlled for adapting to a variety of applications.

The ability to form a desired and predetermined architecture of carbon nanotubes or other nanostructures which are partially embedded and stabilized within a flexible polymer matrix according to the invention may also provide for flexible skin-like materials which may be used as coverings or coatings in a variety of environments and applications. For example, electrodes may be formed having these composite materials incorporated therein for significantly increasing the surface area or providing other significant benefits. Additionally, it is possible to align the carbon nanofibers and selectively expose a portion to form coatings which may have significant properties such as anti-friction, anti-static, or non-wetting surfaces. For various embodiments, it may be useful to form the nanostructure architecture such that individual carbon nanostructures are tangled around adjacent carbon nanostructures (especially at their exposed ends). Such tangling may provide surface unevenness which may increase the surface area of contact with a surface or provide other benefits for certain applications. Alternatively, such unevenness may be provided by forming the nanostructures to have different heights among the various individual carbon nanostructures.

Although the above examples describe the use of multi-walled carbon nanotubes, other carbon nanostructures may be used in accordance with the invention. Similarly, although the polymer used in the example is a glassy PMMA, other elastomeric polymers with different moduli and flexibility may be used for other applications as contemplated in the invention. The ability to use various polymers provides flexibility to tailor the flexible substrate produced for any desired application. Chemical properties may also be controlled as desired for various applications.

Figure 6:
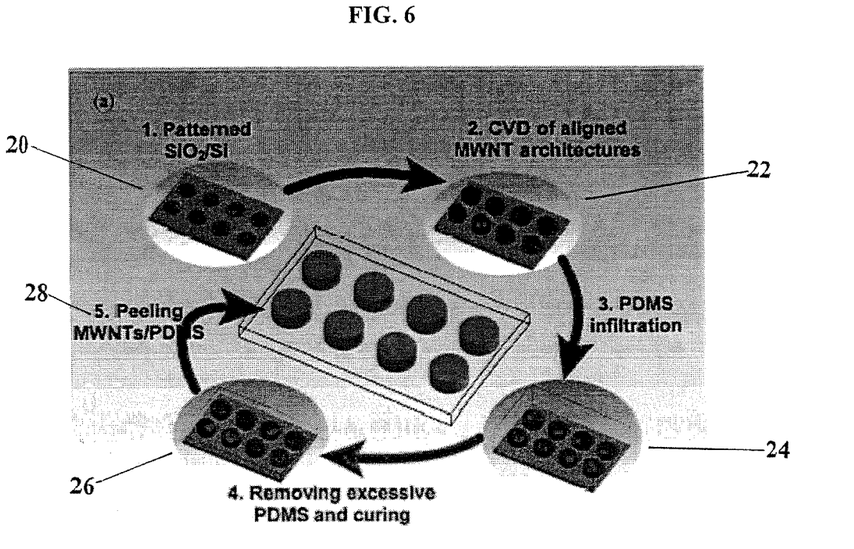
FIG. 6 is a schematic illustration of a further method of forming carbon nanotube-polymer composites according to the invention.
Figure 7:
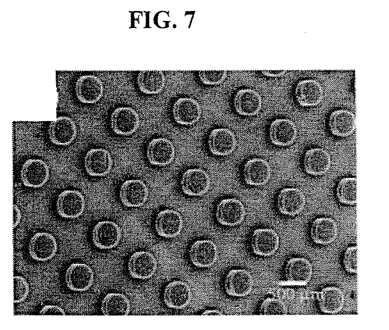
FIG. 7 shows a scanning electron microscope image of the carbon nanotube architectures before being embedded into a polymer matrix.
Figure 8:
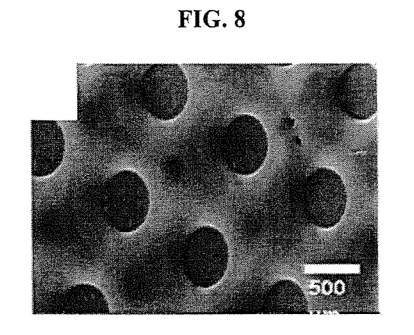
FIG. 8 is a scanning electron microscope image showing the nanotube architectures of FIG. 7 after polymer infiltration.
Figure 9:
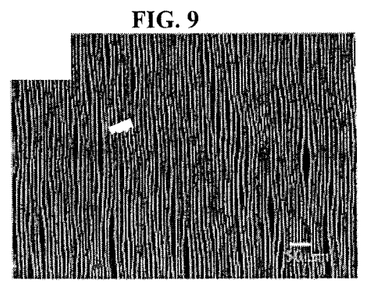
FIG. 9 is a top view of nanotube walls prior to polymer infiltration.
Figure 10:
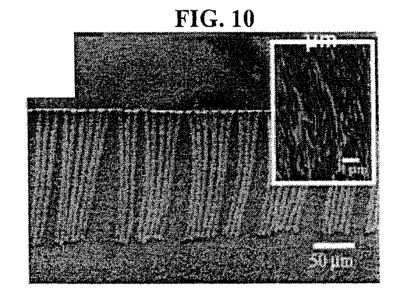
FIG. 10 shows a cross-sectional scanning electron microscope image of the nanotube walls shown in FIG. 9 after polymer infiltration.

Turning now to FIG. 6, a further embodiment of fabricating a carbon nanotube array structure in conjunction with a polymeric substrate is shown. As a first step, similar to that previously described, a prepatterned silicon substrate 20 has bundles of MWNT grown thereon using thermal CVD of Ferrocene and Xylene at 800° C., to form an array of vertically aligned patterned MWNT on the substrate at 22. In this example, a polymer, such as PDMS may be utilized for embedding the MWNT architectures so as to stabilize and fix the MWNT in position. A PDMS prepolymer solution, which may be a viscous mixture of base/curing agent, such as in a weight ratio of 10:1, may be poured over the aligned nanotube structures on the substrate at 24. The arrays of nanotubes are embedded within the soft polymer matrix without disturbing the shape, size or alignment of the nanotubes. Although a particular architecture of aligned MWNT architectures is shown in this example, it should also be recognized that any desired architecture may be easily formed in a similar manner. In this example, subsequent to embedding the nanotube structures on the substrate within the soft prepolymer solution, any excessive polymer solution may be removed to obtain a desired thickness for the nanotube-PDMS composite film being produced. Again in this manner, the particular thickness of the composite film may be controlled for optimizing the arrangement for a particular application or environment (at 26). The PDMS is then thermally cured and, subsequently, self-standing nanotube-PDMS composite films may simply be peeled off from the silicon substrate at 28. This process has been used to make nanotube-PDMS composite films, wherein FIG. 7 shows a tilted SEM image of an array of cylindrical pillars of selectively grown and aligned MWNT structures on a substrate. In this example, the diameter of the MWNT structures may be in the range of 1-500 µm using photolithography. In FIG. 8, the surface morphology of these nanotube pillars is shown after PDMS infiltration, and subsequent completion of polymerization. It has been found in this process, that it is possible to transfer smaller and more densely distributed nanotube architectures into the PDMS matrix, such as structures only a few micrometers in scale. Further, these structures have been shown to effectively retain their original alignment, shape, and size inside the resulting composite matrix, after polymerization and subsequent to peeling off from the substrate. An alternative nanotube structure is shown in FIG. 9, wherein nanotube walls are grown on the substrate, wherein the walls may have desired width, height and spacing between walls. In FIG. 10, a cross-sectional SEM image of the nanotube walls shown in FIG. 9 show that these structures are retained subsequent to infiltration by the PDMS and polymerization thereof. To facilitate this, the selected polymeric materials may be chosen to provide conformal filling of the spaces between individual nanotubes and building blocks thereof in an effective manner. If desired, other chemical agents may be used or polymeric materials chosen to enhance wettability relative to the nanotube architectures to form a relatively defect-free composite film retaining the original nanotube architecture.

Figure 11A:
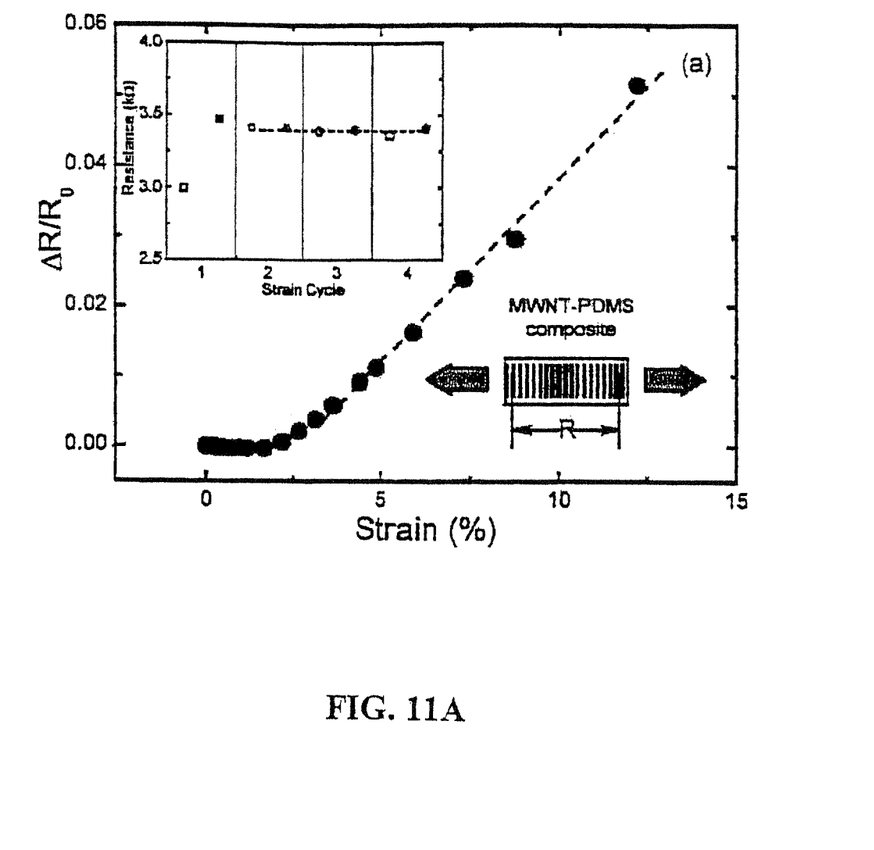
FIGS. 11A and 11B show graphs of electrical resistance of a nanotube-polymer composite structure such as formed according to FIG. 6, relative to strain and compression.
Figure 11B:
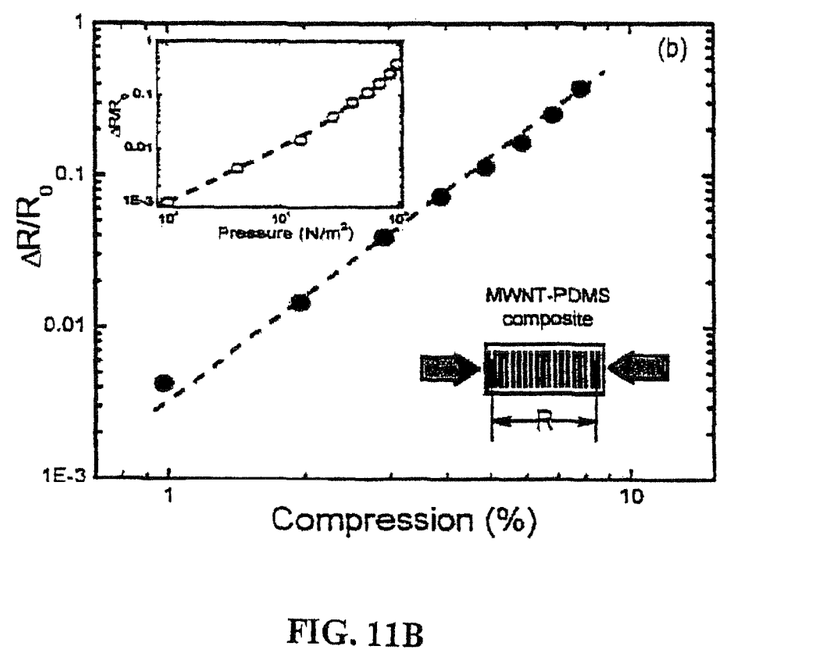

The composite films formed according to the invention provide an extremely flexible and otherwise deformable matrix which may allow the film to be produced in any of a variety of desired configurations and geometries, while maintaining a nanostructure architecture therein. Further, it was found that the composite films according to the invention provide stable electromechanical structures, which enable useful electronic applications. The composites having nanotubes architectures embedded therein are conducting, and sustain the conducting character over large percentages of strain imposed upon the flexible composite. Measurements of resistance as a function of tensile and compressive strains, with deformation and resistance measurements conducted perpendicularly to the alignment of nanotubes in a composite sample are shown in FIGS. 11A and 11B. FIG. 11A shows the typical variation of the normalized composite resistance according to this embodiment, under an applied tensile strain. The inset graph of FIG. 11A shows a summary of the zero strain conditions before and after each strain cycle. As seen, the resistance scales generally linearly beyond a small strain value (approximately 2.5%). The inset graph shows the change in zero-strain resistance before a strain cycle as indicated by the open markers in the graph, and after a strain cycle as indicated by the solid markers in the graph. This summary generally shows that there was an irreversible increase in normalized resistance of approximately 10-15% after the first strain cycle, which thereafter stabilizes over multiple strain cycles.

FIG. 11B shows the normalized resistance as a function of compression, with the values shown as a "log-log" plot showing the normalized resistance during compressive strain cycles. The inset graph of FIG. 11B again shows the summary of the zero-strain resistance both before and after each strain cycle in the testing. As can be seen in FIG. 11B, the normalized resistance increases in general following a power-law dependence on strain. The inset graph shows the device can detect very small changes in pressure of the compressive strain, such as for example in the range of approximately 1000 N/m$^2$.

For these examples, a sample of composite material was provided having a length of 1-2 centimeters, a width of 1-2 millimeters, and a height of approximately 100 µm. Titanium wires were embedded into the composite matrix during curing of the polymer to obtain electrical contacts. The zero-strain lateral resistivity of the composite material varied between 1-10 Ω-cm for various samples, and increased monotonically for both tensile and compressive strains. The aligned nanotube architecture provides a lateral network of conducting fibers, which are connected to each other, and provide a conducting path through the material. Tensile and compressional forces may change the contact area between neighboring filaments to produce variances in accompanying electrical properties. For example, based upon the resistance characteristics from strains imposed upon the composite material, applications of these structures as strain and pressure/touch sensors is contemplated. Further, based upon the conducting nature of the carbon nanotubes under strain, flexible electronic requirements may be provided, such as a flexible cathode for an integrated field-emission device (FED). The high aspect ratio of the carbon nanotubes or other nanostructures and electrical conducting characteristics, would allow use in field emission technologies such as a field emission display devices.

Figure 12:
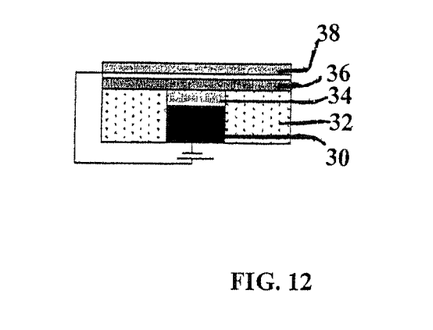
FIG. 12 shows a schematic illustration of a flexible Field Emission Display (FED) using carbon nanotube/polymer composites according to the invention.

As shown in FIG. 12, a flexible/plastic field-emission display may be provided using the composites according to the invention. Carbon nanotube structures may be patterned on a rigid glass substrate, with different colors obtained using phosphorous technology. The schemes of transferring the patterns into and onto a polymer surface can then be used to prepare CNT cathodes wherein a bundle of carbon nanotubes 30 is embedded within insulating polymer 32 according to the invention. An electron transporting layer 34 is provided on top of the CNT bundle, with a layer of phosphorous or LED polymers 36 disposed on the top of the composite material. A protective plastic layer 38 may be provided, with electrical contacts made to the cathode assembly. The flexible interconnect layer 34 may be integrally formed into the assembly if desired, and the polymer matrix itself may incorporate phosphorous-based materials or LED polymers to reduce the need for providing such materials otherwise. Patterns may be disposed on the polymer substrates using soft lithography or other suitable techniques. As it is possible to control the roughness, etching and length of the carbon nanotubes, depending upon the display application, the cathode may be optimized for efficient field-emission. In addition, the chemistry may be optimized to obtain high efficiency of light emission. It is contemplated that flexible displays according to the invention may be used for a variety of applications, including, high definition displays for television, portable newspapers and magazines, head gear for military or entertainment applications, cell or smart phones, PDA's and many other applications.

As an example, testing of field-emission properties was performed on samples of composite materials according to the invention. As shown in FIG. 6, a patterned MWNT-PDMS composite is formed in a cylindrical shape, such as having a diameter of approximately 500 µm. It has been found that adjusting the quantity of PDMS in fabricating the composite allow films to be produced with few or no exposed nanotubes on the top surface of the composite, while the bottom surface of the pattern, where the ends of the nanotubes were completely exposed, was coated with a Ti/Au material and fixed to a metal electrode using a conducting silver paint or the like, thereby forming a composite cathode. A metal anode with an adjustable separation distance was positioned parallel to the top surface of the MWNT-PDMS composite, and the gap therebetween was adjustable. As a possible preconditioning step, high currents may be run through the cathode/anode arrangement, to cause any long or entangled masses of nanotubes to be burnt off while retaining desired length and separation of nanotubes on the top surface of the film composite. Field-emission measurements were performed under a vacuum of approximately $5 \times 10^{-4}$ Torr. When the effective electric field around a nanotube tip exposed on the surface is large enough to overcome the work function of the nanotube (typically estimated at about 5 eV for carbon nanotubes), field emission will occur. The emitted current follows a known mechanism, called the Fowler-Nordheim mechanism, where the current density is approximately related to the effective field through the equation:

$$J_{FN}=(e^3F^2/8\pi h\phi)\exp[-(8\pi\sqrt{(2m)}/3he)(\phi^{3/2}/F)],$$

wherein F is the effective electric field seen by the emitting region, and $\phi$ is the work function of the nanotube. If the separation distance is d, then the field-enhancement factor, $\beta$, is the ratio between the effective field and the applied field, set forth as:

$$\beta=F/(V/d),$$

where V is the applied voltage across the device electrodes. Further, if the effective surface area of the emission is denoted $\alpha$, then the measured current is given by:

$$I=\alpha J_{FN}.$$

This expression can be written as:

$$\ln(I/V^2)=\ln C_1 - C_2/V, \text{ where, } C_1=(e^3/8\pi h d^2\phi)\beta^2\alpha \text{ and } C_2=(8\pi d\phi^{3/2}\sqrt{(2 m)}/3he)(1/\beta).$$

Figure 13:
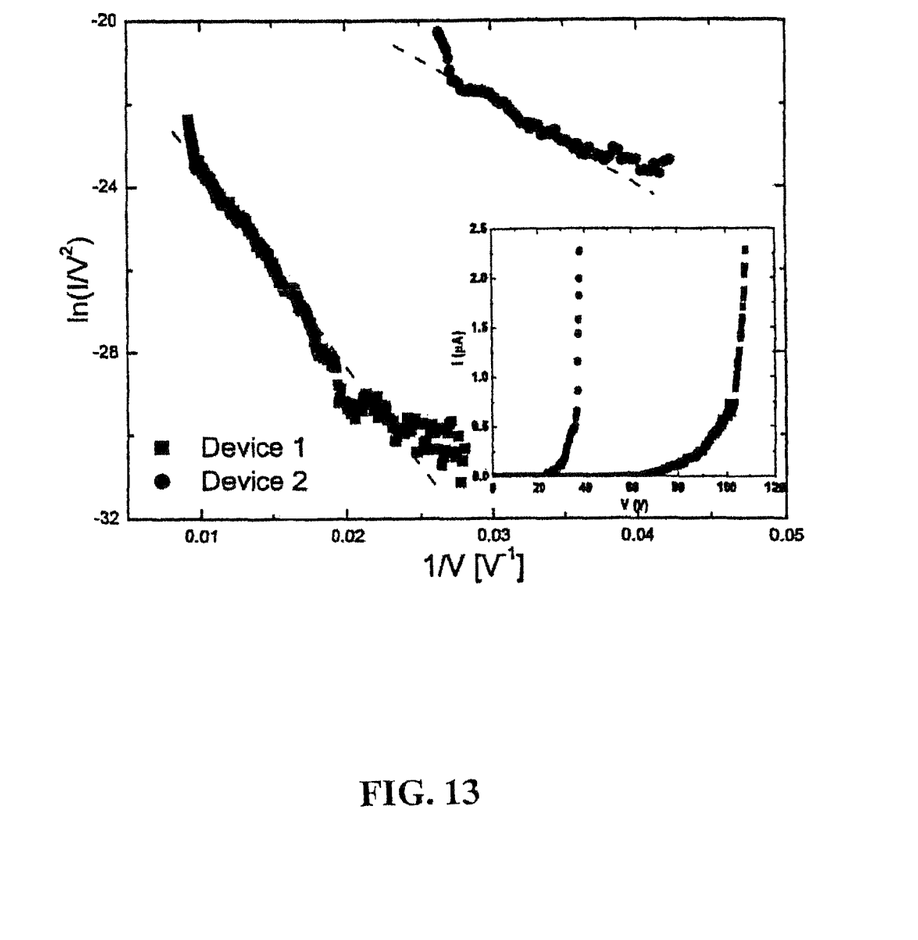
FIG. 13 shows a Fowler-Nordheim plot of field emission, with the inset graph showing emission current for applied voltages for several nanotube-polymer composites according to the invention.

As shown in FIG. 13, a Fowler-Nordheim (FN) plot shows the relationship of ln ($I/V^2$) versus 1/V. The characteristics of two samples devices are shown, with the inset graph showing the emission current for applied voltage for each sample. From the Fowler-Nordheim plot of FIG. 13, it can be seen that the emission characteristics of the system generally follows the FN equation over a broad range of applied voltages, with slight deviations at the lowest and highest bias values. Such deviations may be associated with instrument insensitivity or at the high value possibly from an enhanced field current due to various factors. From the slope of the FN plots as shown in FIG. 13, a field-enhancement factor, $\beta$, of approximately 8,000 was obtained for Device 1, with a better value of approximately 19,100 for Device 2. Other device properties obtained from the FN plots are set forth in the following Table 1.

TABLE 1

Device Properties Obtained From the Fowler - Nordheim Plots

| Device | Enhancement Factor, $\beta$ | $E_{to}$ (V/µm) | Comments on Current Density |
|---|---|---|---|
| 1 | 8000 | 0.87 | 1 mA/cm² @ 2.16 V/µm |
| 2 | 19100 | 0.5 | 1 mA/cm² @ 0.76 V/µm |

As seen therein, the turn-on fields, $E_{to}$, were calculated for the devices, with the values listed in Table 1 indicating high field emission. A nominal current density of 1 mA/cm² over the entire top surface of a nanotube, was achieved easily at threshold fields of 2.16 and 0.76 V/µm for the samples of devices made according to the invention. These values can be reduced by patterning smaller-diameter pillars. Further electrical isolation of the emitting nanotubes from neighboring nanotubes may be provided by use of a dielectric material or insulator therebetween to improve field emission characteristics. As an example, in the samples of field emitters according to the invention, the devices formed had very few tips exposed above the PDMS surface, and those nanotubes that were exposed, had an exposed length of approximately 2 to 3 µm, while being separated by distances of similar or larger lengths. This arrangement was found to decrease mutual screening of the electric fields produced by the nanotubes, and provides large field-enhancement factors with low turn-on fields. The stability provided by embedding the nanotubes within the PDMS matrix prevents movement of the nanotubes with respect to the cathode during high-field operations, providing a well functioning and durable device. For example sub-1 V/µm turn-on fields and threshold fields of a few volts per micrometer may be provided, while remaining stable, flexible and transferable. Such field effect transmission devices may be used for various portable electronic and electro-mechanical devices or other applications.

A field emission display according to the invention may then be formed using the flexible FED as shown in FIG. 12 as an example. As the composite systems are shown to have very efficient electron emission, this may be used to provide a large screen display based on FED technology. Carbon nanostructures on a flexible plastic substrate can provide significant advantages in manufacturing of flexible displays for various applications as previously noted.

Figure 14:
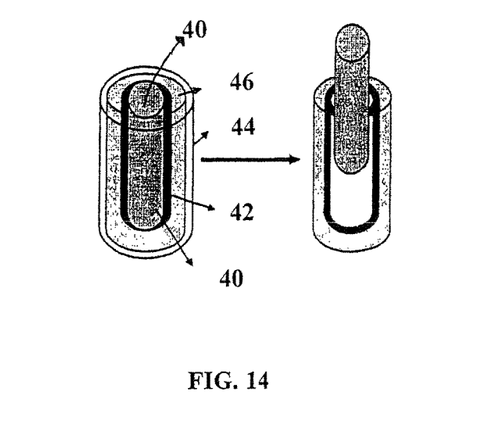
FIG. 14 shows a schematic illustration of a bioactive composite for use in a biological system formed according to an embodiment of the present invention.

In another application according to the invention, a bioactive or biocompatible coating may be formed using nanotubes disposed in a polymer matrix. Such a coating may be formed integrated with a polymer and formed to simulate macroscopic objects such as synthetic blood vessels, stents, membranes for dialysis, and other components, which may be exposed to blood or other biological materials. As shown in FIG. 14, a method of forming carbon nanotubes on the inside of a polymer/nanotube composite capillary is shown, wherein a glass rod or other suitable substrate 40 has carbon nanotubes 42 grown over its exterior surface. The rod with carbon nanotube fibers grown thereon may then be disposed in a larger diameter capillary 44. The annulus surrounding the glass rod 40 with carbon nanotubes 42 disposed thereon is then filled with a suitable monomer or other polymer precursor material 46, and polymerization is accomplished in any suitable manner, such as by the application of heat or the like. The polymer layer 46 is then disposed completely around the glass rod 40 and carbon nanotubes 42 formed thereon, thereby embedding the nanotubes in the polymer matrix. After polymerization, the glass rod 40 can be removed and polymeric tubes with CNT embedded therein are formed. In an example, a desired length of the embedded nanotubes is selectively exposed so as to enable contacting a biological fluid disposed or flowing through the capillary. It is also possible to functionalize the inside of the capillaries with fluorinated monolayers to simplify the removal of the glass rod from a finished tube. Further, it is possible to provide additional chemical properties by use of different monomers and cross-linking groups to prepare elastomers having desired mechanical strengths or other properties. The carbon nanotube surface exposed on the interior of the capillary may have various beneficial applications, such as a coating to prevent inflammatory response, or as a stimulus for cell growth using electrical currents for tissue engineering. Although the formation of a synthetic blood vessel or capillary is shown, a similar approach may be used for providing carbon nanotube architectures in any shape which needs to be replicated for biological applications. The flexibility of the use of various polymer materials, as well as the ability to combine chemical characteristics in association with the polymer matrix and embedded nanotube structure, provides a great amount of flexibility in adapting the composites for various applications.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected. Additional features of the invention will become apparent to those skilled in the art upon consideration of the description. Modifications may be made without departing from the spirit and scope of the invention.

What is claimed is:

1. A carbon nanostructure/polymer composite material comprising:
a plurality of carbon nanostructures having substantially opposed ends formed into a predetermined architecture that includes a hierarchical structure in which larger structures are combined with smaller structures,
the carbon nanostructures architecture configured such that one end of each said plurality of carbon nanostructures is embedded within a polymer matrix that is formed as an elongated tube, said plurality of carbon nanostructures extending from said polymer matrix in a manner that the predetermined architecture is stabilized in said polymer matrix, the other end of each said plurality of carbon nanostructures forming said hierarchical structure is exposed above said polymer matrix and proximate to a cavity formed by said elongated tube.

2. The carbon nanostructure/polymer composite material of claim 1, wherein the predetermined architecture comprises a plurality of nanostructures which include the combination of micron-size structures formed by bundles or groups of nanostructures, and nanometer-size structures formed by one or more individual nanostructures.

3. The carbon nanostructure/polymer composite material of claim 2, wherein the micron-size structures formed by bundles or groups of nanostructures vary from about 50 to 500 microns in width.

4. The carbon nanostructure/polymer composite material of claim 3, wherein the micron-size structures formed by bundles or groups of nanostructures are spaced from one another a distance varying in a range from about 5-500 µm.

5. The carbon nanostructure/polymer composite material of claim 2, wherein the nanometer-size structures formed by one or more individual nanostructures vary from about 1 to 30 nanometers in width.

6. The carbon nanostructure/polymer composite material of claim 2, wherein the nanostructures are exposed above the surface of the polymer matrix with the height of exposed ends of the nanostructure extending above the surface of the flexible polymer matrix in the range from about 10 µm-1000 µm.

7. The carbon nanostructure/polymer composite material of claim 1, wherein the predetermined architecture is formed by patterning by photolithography followed by etching in order to create various predetermined patterns of the carbon nanostructures.

8. The carbon nanostructure/polymer composite material of claim 1, wherein the hierarchical structure includes micron-size structures formed by bundles or groups of nanostructures, and nanometer-size structures formed by one or more nanostructures.

9. The carbon nanostructure/polymer composite material of claim 1, wherein the hierarchical structure includes patterning of nanostructures having surface areas of about 0.16 $cm^2$ and 0.25 $cm^2$.

10. The carbon nanostructure/polymer composite material of claim 1, wherein the nanostructure architecture is formed such that the individual carbon nanostructures are tangled around adjacent carbon nanostructures to provide surface unevenness and increase surface contact area.

11. The carbon nanostructure/polymer composite material of claim 1, wherein the architecture is formed to have surface unevenness by forming the nanostructures to have different exposed heights among the various individual carbon nanostructures.

12. The carbon nanostructure/polymer composite material of claim 1, wherein the architecture is formed as a plurality of carbon nanostructure walls, wherein the walls have a predetermined spacing between walls.

13. The carbon nanostructure/polymer composite material of claim 1, wherein the architecture is formed as a plurality of pillars of nanostructures, with the diameter or width of the nanostructures in the range of about 1-500 µm.

14. The carbon nanostructure/polymer composite material of claim 6, wherein the carbon nanostructures extend from the surface of the polymer matrix an amount of less than 200 micrometers.

15. The carbon nanostructure/polymer composite material of claim 1, wherein the carbon nanostructures are partially embedded and stabilized using a molten interface.

16. The carbon nanostructure/polymer composite material of claim 1, wherein the carbon nanostructures are partially embedded and stabilized using a prepolymer, wherein a paste of prepolymer is provided and carbon nanostructures are brought in contact with the surface so that only a part of carbon nanostructures are embedded inside the prepolymer, with the prepolymer then being cross-linked to trap one end of carbon nanostructures in its matrix.

17. The carbon nanostructure/polymer composite material of claim 1, wherein the carbon nanostructures are partially embedded and stabilized using a monomer, with the carbon nanostructures brought into contact with the monomer and thereafter causing polymerization of the monomer so that only a part of carbon nanostructures are embedded inside the resulting polymer material.

18. The carbon nanostructure/polymer composite material of claim 1, wherein the carbon nanostructures are partially embedded and stabilized using a degradable substance capable of degrading under predetermined conditions which is used to coat the carbon nanostructures with a thin layer, and thereafter exposing the matrix to suitable conditions to cause degradation of a portion of the degradable substance thereby leaving a portion of the carbon nanostructures extending from the surface.

19. The carbon nanostructure/polymer composite material of claim 1, wherein said polymer matrix is flexible.

20. The carbon nanostructure/polymer composite material of claim 1, wherein said polymer matrix is rigid.

* * * * *